US00PP33252P3

(12) United States Plant Patent
Larse

(10) Patent No.: US PP33,252 P3
(45) Date of Patent: Jul. 13, 2021

(54) STRAWBERRY PLANT NAMED 'SHANNON M. KENT'

(50) Latin Name: ***Fragaria* x *ananassa***
Varietal Denomination: Shannon M. Kent

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 16/873,474

(22) Filed: Apr. 17, 2020

(65) Prior Publication Data

US 2020/0337191 P1 Oct. 22, 2020

Related U.S. Application Data

(60) Provisional application No. 62/835,705, filed on Apr. 18, 2019.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208
See application file for complete search history.

(56) References Cited

U.S. PATENT DOCUMENTS

| | | | |
|---|---|---|---|
| PP7,614 | P | 8/1991 | Bringhurst et al. |
| 2020/0337192 | P1 | 10/2020 | Larse |
| 2020/0337193 | P1 | 10/2020 | Larse |

*Primary Examiner* — Susan McCormick Ewoldt
*Assistant Examiner* — Karen M Redden
(74) *Attorney, Agent, or Firm* — Cooley LLP

(57) ABSTRACT

The present invention provides a new and distinct strawberry variety designated as 'Shannon M. Kent' (a.k.a. '110168'). The 'Shannon M. Kent' cultivar is primarily adapted to growing conditions of the central coast of California and produces strong vigorous plants that remain in fruit production from March through October.

3 Drawing Sheets

Latin name of the genus and species: *Fragaria* x *ananassa.*

Varietal denomination: 'Shannon M. Kent'.

BACKGROUND OF THE INVENTION

The present invention relates to a new and distinct strawberry variety designated as 'Shannon M. Kent' (a.k.a. '110168'), which was previously designated 'Perla', as disclosed in U.S. Provisional Patent Application No. 62/835,705.

'Shannon M. Kent' (a.k.a. '110168') is the result of a controlled-cross between a female parent cultivar designated '107987' and a male parent cultivar designated '107801', and was first fruited in Watsonville, Calif. growing fields. Both parents are proprietary strawberry plant varieties made by the inventor and are not available to the public. Following selection and during testing, the plant was originally designated '110168' and subsequently named 'Shannon M. Kent'.

This new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar is stable and reproduce true to type in successive generations of asexual reproduction.

DESCRIPTION OF THE DRAWINGS

The accompanying color photographs depict various characteristics of the cultivar as nearly true as possible to make color reproductions. The age of the plants in FIGS. 1-3 is nine months old.

SUMMARY OF THE INVENTION

Figure 1:
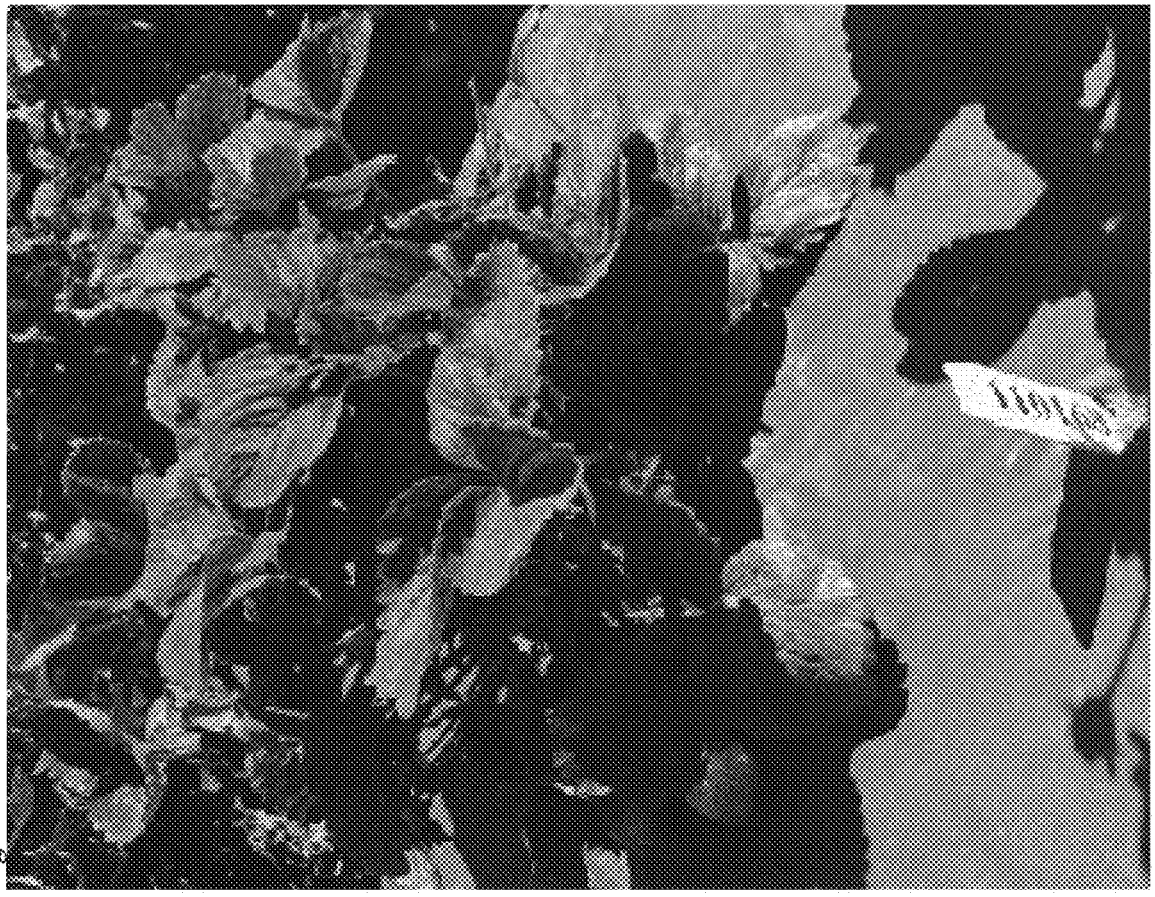
FIG. 1 shows 'Shannon M. Kent' plant.
Figure 2:
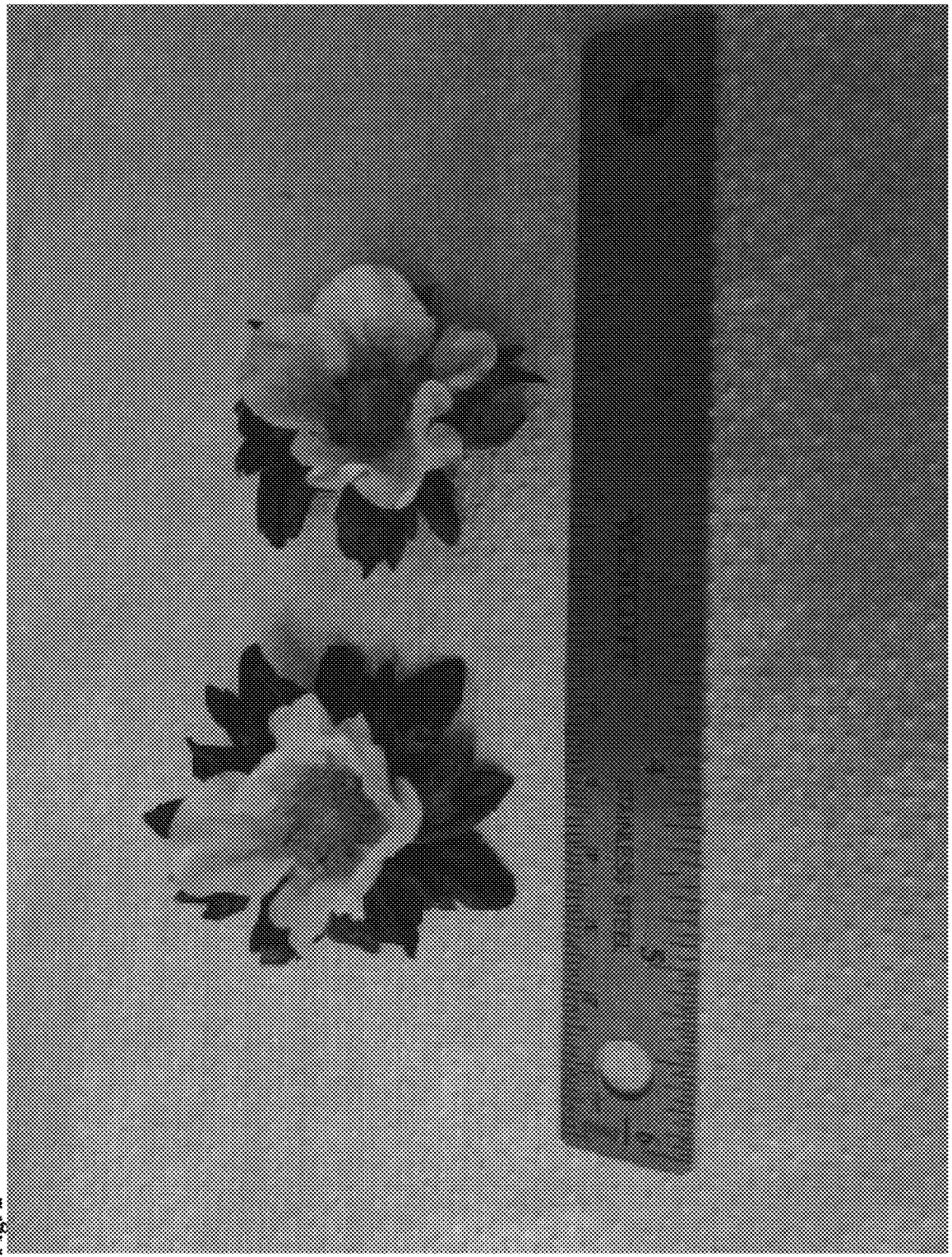
FIG. 2 shows 'Shannon M. Kent' flowers.
Figure 3:
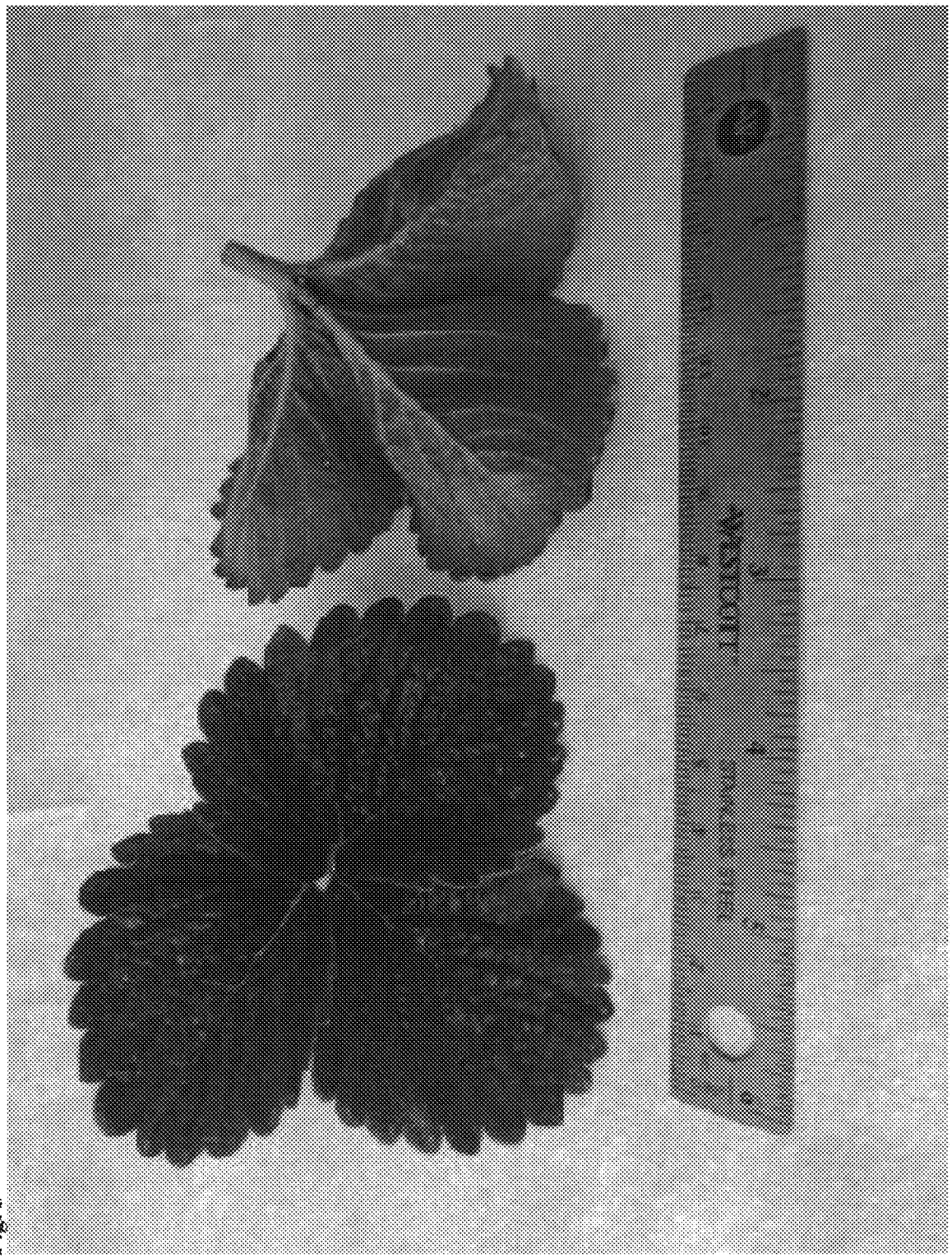
FIG. 3 shows 'Shannon M. Kent' leaf.

This invention relates to a new and distinctive strawberry cultivar designated as 'Shannon M. Kent' (a.k.a. '110168'). This cultivar is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish the strawberry variety 'Shannon M. Kent' from known strawberry varieties. Plants for the botanical measurements in the present application were grown as annuals. Any color references are made to The Royal Horticultural Society Colour Chart, 1995 Edition, except where general terms of ordinary dictionary significance are used. The age of the plants in Table 1 is nine months old.

TABLE 1

Characteristics of Shannon M. Kent

| Characteristic Type | Characteristic | Observation |
|---|---|---|
| General | Plant Habit | annual |
| | Plant Growth Habit | semi-upright |
| | Day length | neutral |
| | Planting season | Fall |
| | Height | 30.5 cm |
| | Width | 38.5 cm |
| | Density of foliage | medium |
| | Plant vigor | moderate |
| | Freezing Quality | moderate |
| | Rain/weather tolerance | moderate |
| | Harvest Ease | moderate |
| Leaf | Number of leaflets per leaf | 3 |
| | Leaflet texture | soft |
| | Leaf average width, | 142 mm |
| | Leaf average height | 76 mm |
| | Leaf Shape | concave |
| | Terminal leaflet width | 76 mm |
| | Terminal leaflet length | 69 mm |
| | Terminal leaflet length/width ratio | 1.1 |
| | Teeth per terminal leaflet | 24 to 27 |
| | Shape of the terminal leaflet base | obtuse to rounded |
| | Shape of terminal leaflet in cross-section | concave |
| | Shape of the terminal leaflet margin | serrate to crenate |
| | Color of upper side of leaflet | RHS 137A |
| | Color of lower side of leaflet | RHS 137C |
| | Leaf blistering | weak |
| | Leaf glossiness | medium |
| | Leaf variegation | absent |
| | Terminal Leaflet margin | flat to revolute |
| | Terminal Leaflet shape | orbicular |
| | Terminal Leaflet shape of apex | rounded |
| Limbs | Petiole length | 21.2 cm |
| | Petiole diameter | 3.65 mm |
| | Petiole pubescence | medium |
| | Petiole pose of hairs | slightly outwards |
| | Petiole color | RHS 145B |
| | Petiolule length | 0.4 to 0.7 cm |
| | Petiolule diameter | 2.00 to 3.33 mm |
| | Petiolule color | RHS 139D |
| | Stipule length | 3.8 cm |
| | Stipule width | 1.0 cm |
| | Stipule pubescence | medium |
| | Stipule anthocyanin | present |
| | Stipule color | RHS 145A |
| | Peduncle average length | 15.2 cm |
| | Peduncle average diameter | 4.88 mm |
| | Peduncle color | RHS 145B |
| | Pedicel average length | 8.12 cm |
| | Pedicel average diameter | 3.1 mm |
| | Attitude of hairs on peduncle and pedicel | upwards |
| Inflorescence | Inflorescence position relative to foliage | above |
| | Flower arrangement of petals | touching to overlapping |
| | Flower size | medium to large |
| | Flower diameter | 3.5 to 3.9 cm |
| | Petal shape | orbicular |
| | Petal apex | rounded |
| | Petal margin | entire |
| | Petal base shape | concave |
| | Petal length | 2.0 cm |
| | Petal width | 2.0 cm |
| | Petal length/width ratio | 1 |
| | Petal number per flower | 6 |
| | Upper Petal color | RHS 155C |
| | Lower Petal color | RHS 155C |
| | Peduncle size | medium |
| | Floral Calyx Diameter | 5.0 to 5.6 cm |
| | Corolla diameter | 3.5 to 3.9 cm |
| | Calyx diameter relative to corolla | larger |

TABLE 1-continued

Characteristics of Shannon M. Kent

| Characteristic Type | Characteristic | Observation |
|---|---|---|
| | Inner calyx diameter relative to outer calyx | equal to smaller |
| | Sepal shape | elliptical |
| | Sepal apex | convex |
| | Sepal margin | entire |
| | Sepal length | 2.6 cm |
| | Sepal width | 1.1 cm |
| | Sepal number per flower | 14 |
| | Fertility | not tested |
| | Time of flowering (50% of plants in bloom) | May |
| | Stigma shape | capitate |
| | Stigma color | RHS 15B |
| | Style length | 1.5 mm |
| | Style color | RHS 6A |
| | Ovary color | RHS 145A |
| | Number of stamen | 25 to 30 |
| | Stamen length | 3.0 to 6.0 mm |
| | Anther shape | dorsifixed |
| | Anther size | 1.5 mm |
| | Anther color | RHS 22A |
| | Filament color | RHS 8C |
| | Filament length | 2.5 to 5.5 mm |
| Stolon | Number of Stolon | 3 |
| | Stolon length | 45 cm |
| | Stolon widest diameter at leaf attachment | 3.6 mm |
| | Stolon texture | smooth |
| | Stolon pubescence | sparse |
| | Stolon shape | long cylindrical |
| | Stolon color | RHS 142A |
| | Stolon anthocyanin intensity | Absent |
| Fruit | Average number of fruits per truss | 5 |
| | Fruit length | 4.15 cm |
| | Fruit width | 4.15 cm |
| | Fruit length/width ratio | 1 |
| | Fruit weight | 26.5 g |
| | Firmness of flesh | firm |
| | Relative fruit size | medium to large |
| | Predominant fruit shape | globose conic |
| | Achenes position | slightly indented |
| | Achenes color full ripe | RHS 154D |
| | Achenes color near ripe | RHS 43B |
| | Achenes number per fruit | about 280 |
| | Fruit skin color | RHS 44B |
| | Fruit flesh color | RHS 44B |
| | Fruit core color | RHS 43B |
| | Calyx color | RHS 137A |
| | Pose of calyx segments | reflexed |
| | Flesh firmness | firm |
| | Sweetness | 7.11 Brix |
| | Acidity | 3.49 pH |
| | Time of flowering | May |
| | Time of fruit ripening | May |
| | Harvest maturity (50% of plants with ripe fruit | June |
| | Type of bearing | day neutral |
| | Surface Texture | smooth |
| | Fruit Appearance (1-7 scale; 7 = best) | 6 |
| | Storage longevity | 10 days |
| | Percent marketable fruit | 85% |
| Horticultural | Average plant marketable fruit yield (weeks 17-37) | 1476 g |
| | Crop suitability | Fresh market and freezer |
| | Temperature tolerance range | −2° C. to 36° C. |
| | USDA Hardiness Zone adaptability for annual transplanting of California grown commercial rootstock | 5a,5b,6a,6b,7a,7b, 8a,8b,9a,9b, 10a |
| | Cull rate (% Usable) | 14.5% |

'Seascape' (U.S. Plant Pat. No. 7,614) is a commercial strawberry variety that is similar to, but distinguished from 'Shannon M. Kent'. The fruit yield 'Shannon M. Kent' is greater than the fruit yield of comparison variety 'Seascape' and 'Shannon M. Kent' has a greater percent of marketable fruit than 'Seascape'. The fruit height to fruit width ratio of the fruit of 'Shannon M. Kent' closer to unity compared to the fruit height to fruit width ratio of the fruit of 'Seascape'. The petiole of 'Shannon M. Kent' is thicker in diameter than the petiole of 'Seascape'. The florescence of 'Shannon M. Kent' extends beyond the leaf canopy and 'Shannon M. Kent' is easier to harvest compared to 'Seascape' with its habit of setting fruit beneath the canopy.

The new strawberry variety 'Shannon M. Kent' exceeds both its parents in fruit yield and the percent of marketable fruit of 'Shannon M. Kent' is less than the percent marketable fruit of female parent '107987' and greater than that of male parent '107801'. The full fruiting season fruit yield of 'Shannon M. Kent' is greater than the yield of male parent '107801', however, the male parent produced more fruit during the early season when compared to 'Shannon M. Kent'. The fruit of 'Shannon M. Kent' is firmer than male parent '107801'. The fruit colour of 'Shannon M. Kent' is deeper red than the fruit colour of either of its two parents.

The invention claimed is:

1. A new and distinct cultivar of strawberry plant named 'Shannon M. Kent' substantially as shown and described herein.

* * * * *